US008998972B2

(12) United States Patent  
Smirthwaite et al.

(10) Patent No.: US 8,998,972 B2  
(45) Date of Patent: Apr. 7, 2015

(54) FLEXIBLE STENT-GRAFT

(75) Inventors: Amie Smirthwaite, Didcot (GB); Duncan Keeble, Didcot (GB); Peter William Philips, Didcot (GB)

(73) Assignee: Anson Medical, Ltd. (GB)

( * ) Notice: Subject to any disclaimer, the term of this patent is extended or adjusted under 35 U.S.C. 154(b) by 1414 days.

(21) Appl. No.: 10/526,418

(22) PCT Filed: Sep. 3, 2003

(86) PCT No.: PCT/GB03/03809  
§ 371 (c)(1),  
(2), (4) Date: Oct. 21, 2005

(87) PCT Pub. No.: WO2004/019819  
PCT Pub. Date: Mar. 11, 2004

(65) Prior Publication Data  
US 2006/0149351 A1   Jul. 6, 2006

(30) Foreign Application Priority Data  
Sep. 2, 2002   (GB) .................................. 0220340.4

(51) Int. Cl.  
*A61F 2/86* (2013.01)  
*A61F 2/07* (2013.01)  
*A61F 2/89* (2013.01)

(52) U.S. Cl.  
CPC ........... *A61F 2/07* (2013.01); *A61F 2250/0039* (2013.01); *A61F 2/89* (2013.01); *A61F 2002/075* (2013.01)

(58) Field of Classification Search  
CPC ... A61F 2/07; A61F 2002/91541; A61F 2/86; A61F 2002/075

USPC ................................................. 623/1.11–1.54  
See application file for complete search history.

(56) References Cited

U.S. PATENT DOCUMENTS

| | | | | |
|---|---|---|---|---|
| 4,886,062 A | * | 12/1989 | Wiktor | 606/194 |
| 4,969,458 A | * | 11/1990 | Wiktor | 623/1.11 |
| 5,122,154 A | * | 6/1992 | Rhodes | 623/1.13 |
| 5,246,445 A | * | 9/1993 | Yachia et al. | 623/1.2 |
| 5,330,500 A | * | 7/1994 | Song | 623/1.2 |
| 5,383,892 A | | 1/1995 | Cardon et al. | |
| 5,562,641 A | * | 10/1996 | Flomenblit et al. | 604/531 |
| 5,575,818 A | * | 11/1996 | Pinchuk | 623/1.15 |
| 5,630,829 A | * | 5/1997 | Lauterjung | 623/1.15 |
| 5,693,083 A | * | 12/1997 | Baker et al. | 623/1.11 |

(Continued)

FOREIGN PATENT DOCUMENTS

| | | |
|---|---|---|
| EP | 0 808 614 A | 11/1997 |
| EP | 0808614 A2 | 11/1997 |

(Continued)

*Primary Examiner* — David Isabella  
*Assistant Examiner* — Ann Schillinger  
(74) *Attorney, Agent, or Firm* — Craig A. Fieschko, Esq.; DeWitt Ross & Stevens S.C.

(57) ABSTRACT

A stent graft is provided which has two stent sections having different functions on, for example, a tubular graft. One stent section preferably comprises a plurality of circumferential reinforcing hoops and the other a Z-stent. The two sections are preferably separated by a spacer section and the tubular graft preferably increases in diameter from the Z-stent section to the hooped section. This enables the stent graft to be compressed radially so that it can be inserted in a catheter for later delivery to a body lumen.

29 Claims, 2 Drawing Sheets

(56) References Cited

U.S. PATENT DOCUMENTS

| | | | |
|---|---|---|---|
| 5,741,333 A * | 4/1998 | Frid | 623/1.2 |
| 5,800,508 A * | 9/1998 | Goicoechea et al. | 623/1.15 |
| 5,824,037 A * | 10/1998 | Fogarty et al. | 623/1.13 |
| 5,827,321 A | 10/1998 | Roubin et al. | |
| 5,843,162 A | 12/1998 | Inoue | |
| 5,904,714 A * | 5/1999 | Nunez et al. | 139/383 R |
| 5,993,481 A * | 11/1999 | Marcade et al. | 623/1.35 |
| 6,015,431 A * | 1/2000 | Thornton et al. | 623/1.14 |
| 6,027,525 A * | 2/2000 | Suh et al. | 623/1.1 |
| 6,077,296 A | 6/2000 | Shokoohi et al. | |
| 6,106,548 A | 8/2000 | Roubin et al. | |
| 6,110,198 A * | 8/2000 | Fogarty et al. | 623/1.12 |
| 6,123,115 A * | 9/2000 | Greenhalgh | 139/196.1 |
| 6,123,722 A * | 9/2000 | Fogarty et al. | 623/1.1 |
| 6,159,239 A | 12/2000 | Greenhalgh | |
| 6,164,339 A | 12/2000 | Greenhalgh | |
| 6,192,944 B1 | 2/2001 | Greenhalgh | |
| 6,217,609 B1 * | 4/2001 | Haverkost | 623/1.22 |
| 6,254,632 B1 * | 7/2001 | Wu et al. | 623/1.15 |
| 6,331,190 B1 | 12/2001 | Shokoohi et al. | 623/1.22 |
| 6,334,867 B1 * | 1/2002 | Anson | 623/1.13 |
| 6,338,739 B1 * | 1/2002 | Datta et al. | 623/1.15 |
| 6,355,070 B1 * | 3/2002 | Andersen et al. | 623/23.7 |
| 6,432,134 B1 | 8/2002 | Anson et al. | |
| 6,706,064 B1 | 3/2004 | Anson | |
| 2001/0044647 A1 * | 11/2001 | Pinchuk et al. | 623/1.13 |
| 2002/0058984 A1 * | 5/2002 | Butaric et al. | 623/1.13 |
| 2002/0198587 A1 * | 12/2002 | Greenberg et al. | 623/1.13 |
| 2007/0213806 A1 | 9/2007 | Roubin et al. | |
| 2007/0213807 A1 | 9/2007 | Roubin et al. | |
| 2007/0213808 A1 | 9/2007 | Roubin et al. | |

FOREIGN PATENT DOCUMENTS

| | | |
|---|---|---|
| FR | 2 745172 A | 8/1997 |
| JP | 10043315 A | 2/1998 |
| JP | 2001511044 T | 8/2001 |
| WO | WO 96/36387 A1 | 11/1996 |
| WO | WO 98/34668 A1 | 8/1998 |
| WO | WO 99 37242 A | 7/1999 |
| WO | WO 99/44536 A | 9/1999 |
| WO | WO 00 09059 A | 2/2000 |
| WO | WO 01 30269 A | 10/2000 |

\* cited by examiner

FLEXIBLE STENT-GRAFT

FIELD OF THE INVENTION

The present invention relates to implants for surgery to tubular vessels such as blood vessels, the trachea and bronchus and many parts of the gastro-intestinal tract but is currently of most benefit in surgery to arteries, more particularly those arteries which are susceptible to aneurysmal disease. Such arteries include the aorta, iliac and femoral arteries, although other sites are possible.

BACKGROUND OF THE INVENTION

A number of stent-grafts for treating abdominal aortic aneurysms have been described or manufactured and many of the currently available commercial designs involve the combination of 'Z-stents', similar to the Gianturco (Cook Inc, Indianapolis) and a conventional tubular vascular graft woven from polyester. 'Z-stents' (FIG. 2) are formed from metal wire such that the path of the wire lies on the surface of a cylinder and zig-zags repeatedly between the ends of the cylinder as the wire progresses around the circumference. Usually, the two ends of the wire are joined by welding, crimping or other means to provide a single resilient structure which is of low bulk and is capable both of being compressed radially and of expanding radially once compression forces have been removed.

The characteristics of the 'Z-stent' can be adjusted for any given diameter by controlling the length of cylinder enclosed by the stent, the number of zig-zags made by the wire around the circumference of the cylinder and the physical characteristics of the wire. Further modifications and improvements to the basic design of the Z-stent have been employed, generally to reduce stress at the Z bends in the construction. FIGS. 3 a, b, c and d illustrates variants of bend which have been employed. Struts in Z-stents have also been modified, so that they are curved rather than straight, to permit attachments for barbs or to ease assembly of devices. The present invention applies equally to variants of Z-stents as it does to the basic structure.

Two examples of stent-grafts employing "Z-stents" are the Medtronic 'Talent' device and the Cook "Zenith" device. These implants employ multiple 'Z-stents' which are sewn at intervals along the length of a tubular woven graft in such a way as to hold the graft open and to wedge the assembly within the artery in which it is deployed. The entire assembly can be compressed radially so that it will fit into a delivery catheter, providing the means for introducing the implant into the lumen of a patient's aorta via a minimal incision into the patient's femoral or iliac artery.

The 'Z-stent' is not capable of being flexed along its central axis and is prone to collapse partially when it is flexed. For this reason, stent grafts comprised of 'Z-stents' have limited, segmental flexibility, being inflexible in the regions of the stents and partially flexible at the gaps.

An alternative reinforcing structure to the Z-stent is a tube with perforated walls so that once radially expanded, the tube has roughly diamond-shaped perforations. Such reinforcements are used in the Anneurx product from Medtronic and the Cordis stent graft. The diamond mesh structures are generally stiffer than the wire zig-zags of the Z-stent, limiting the flexibility of the overall structure in which they are used.

SUMMARY OF THE INVENTION

The present applicant has invented structures which are more flexible than the Z-stent or diamond mesh stent. Said structures can be used to support stent grafts and involve wire rings or helices supporting graft material. They allow stent grafts to be used in very much more tortuous vessels than designs using other reinforcements and provide a valuable clinical option.

The materials used for reinforcing structures in stent-grafts are typically metallic and include stainless steel, Elgiloy, titanium and shape memory alloys such as Nitinol. This latter class of material has been used successfully in both the thermal-effect and super-elastic conditions.

In use, stent grafts are compressed and packed into a delivery sheath which is typically ¼ of the diameter of the final device. Z-stents and diamond mesh stents can be compressed radially to this extent, giving rise to a small increase in their overall length.

By contrast, wire hoops are deformed into a saddle shape in which, if the wire is considered to be divided into quadrants, one pair of opposing quadrants is pulled above the plane of the hoop while the other pair of quadrants is pushed below the plane of the hoop.

Clinically, it is often difficult to assess the exact diameter of the vessel into which the stent graft is to be placed and clinicians will often select a stent graft which is larger in diameter than its intended implantation site by typically 15% to 20%, thereby ensuring that the implant is a firm fit. The consequence of this over-sizing is that the neck of the implant will remain partially deformed in a saddle shape, requiring a significant length of healthy tissue over which it is to be attached.

A useful compromise is achieved by combining the standard Z-stent or diamond mesh stent with the wire ring or helical design. Such constructions can be easily envisaged; however, because the two types of support structure deform differently while being packed, it is difficult to combine both structures on a single device.

In a first aspect of the present invention there is provided a stent graft comprising graft material having a first stent section and a second stent section, wherein the first stent section has a different function to the second stent section. Thus the two sections impart different functions to the stent graft.

For example, the two sections can be constructed differently so as to provided different types of support or flexion to the stent graft. Alternatively, one of the sections may have its surface modified chemically or physically (for example to alter its ability to bind or release pharmaceuticals) whereas the other surface may be left unmodified. One of the sections may be adapted to be flexible whereas the other may be adapted to provide a sealing function. Alternatively one section may provide an occluding function.

In a preferred embodiment, a tubular graft is provided having a first stent section comprising reinforcing material formed into a first pattern on the graft and a second stent section comprising reinforcing material formed into a second pattern on the graft wherein the first pattern is different to the second pattern.

The first stent section may comprise a plurality of circumferential hoops of reinforcing material disposed around the tubular graft. Alternatively it may comprise a continuous length of reinforcing material which is disposed around the tubular graft in a pattern which oscillates (or zigzags) about a line which is parallel to the longitudinal axis of the tubular graft as disclosed in WO 99/37242 (in the name of the present applicant), the contents of which are incorporated herein by reference.

The second stent section preferably comprises at least one circumferential hoop of reinforcing material which oscillates (preferably zigzags) about a line running circumferentially around the longitudinal axis of the tubular graft; in other words the second stent section comprises at least one Z-stent.

Other types of stent which may be employed comprise reinforcement material formed into a diamond mesh pattern or a helical pattern as described above. A graft having a helical stent pattern is disclosed in WO 01/30269 in the name of the present applicant (the contents of which are incorporated herein by reference) as are other types of stenting which may be employed. It will be appreciated that the present invention encompasses the use of these various different stent sections in any combination.

In a particularly preferred embodiment the first stent section comprises a plurality of circumferential hoops and the second stent section at least one Z-stent as described above. It will be appreciated that the Z-stent and the circumferential hoops are both annuli, and that the difference between them is that the Z-stent oscillates about the circumferential "mean" whereas the hoops are relatively "flat". However, it is possible for the hoops to oscillate very gently and still retain their function and indeed it is difficult to construct a completely flat hoop. Thus the difference between the hoops and the Z-stent can be defined in terms of the relative amplitude of the oscillation, or equivalently by the ratio between the diameter of the hoop and the distance between the peak of the oscillation and the trough as measured along the longitudinal axis of the graft.

Although the diameter of a tubular graft can range from 3 mm to 60 mm, a more typical range is from 10 to 50 mm and the most commonly used tubular graft has a diameter of about 30 mm. A circumferential hoop of reinforcing material for a graft of 30 mm diameter may have a peak-to-trough distance of preferably no more than 4 mm, more preferably no more than 3 mm, and most commonly 2 mm (although the ideal is a completely "flat" hoop, that is one with a peak-to-trough distance of zero, this is difficult to achieve in practice).

For a tubular graft with a 30 mm diameter the Z-stent of the present invention may have a peak-to-trough distance preferably from 12 to 20 mm, more preferably from 14 to 18 mm and most preferably about 16 mm.

The length separating the peak from the trough in the Z-stent preferably lies in the range 5 mm to 20 mm for stent grafts used in the abdominal aorta or, more generally, lying in the range of a sixth to two-thirds the diameter of the implant. Most preferably, the Z-stent has as short a length as possible to provide the best articulation, although a variety of lengths may be appropriate for different clinical situations.

In a preferred embodiment the stent graft has a single Z-stent disposed at one end of the graft but it will be appreciated that the first and second stent sections may be disposed along any part of the tubular graft.

The design of the Z-stent itself is optimised for combination with the hoop graft. Preferably, the stent has 6 peaks so that when viewed from the Z-stent end, peaks are orientated at 12 o'clock and 6 o'clock while troughs are orientated at 3 o'clock and 9 o'clock. In this way, when the hoop is transformed into a saddle shape, its peaks coincide with the peaks of the Z-stent and its troughs coincide with Z-stent troughs. It will be seen that a Z-stent having 2+4n peaks where n is an integer provides a series of stents with the properties as described. For example, stents have been manufactured where n=1, n=2 and n=3; the case where n=0 is equivalent to a hoop which has been deformed into a saddle shape.

In one embodiment of the invention, the wire forming the Z-stent is run continuously from the Z-stent into the hoop supported section, permitting simplification in manufacture. Preferably, the path taken by the wire as it traverses the interface is oblique to the main axis of the tubular device.

In a preferred embodiment the tubular graft has a different diameter in the region of the first stent section to the diameter of the graft in the region of the second stent section. It is particularly preferred that the graft in the region of the Z-stent have a smaller diameter than that in the region of the circumferential hoops. Although it is possible to construct an implant in which the change in diameter decreases from the Z-stent section, packing is more difficult and the clinical benefits are reduced.

The change in diameter is preferably between 3 and 10 times the thickness of the wall of the graft although if poorer performance can be tolerated, the range can be extended to 2 to 50 times the wall thickness. Thus for a standard graft material which is from 0.1 to 0.5 mm thick the change in diameter is preferably from 0.3 mm to 5 mm.

The feature of the present invention which requires the diameter of the graft to change from the first stent section to the second is not intended to encompass a graft which splits into more than one section, for example which bifurcates or which has a branch tube disposed on the side wall of the main "trunk" of a tubular graft, even though the bifurcated section or the side branch will usually have a smaller diameter than the principal section of the graft. Rather, the change in diameter in the case of the present invention is a change in diameter of a continuous section of tubular graft. Thus the two sections of tubular graft of different diameter are intended to fit in the same continuous body lumen. That is not to say however that the stent graft of the present invention may not have a bifurcated section or a side branch somewhere on the graft; it is just that the change in diameter discussed above is a change in a unbifurcated section.

The first and the second stent sections are preferably separated by a spacer section which is a region of tubular graft which does not have any stent. The spacer section is preferably between a third and a sixth of the diameter of the graft but in some circumstances can lie in the range of a tenth to a half of said diameter. Its function is to provide some articulation between the Z-stent and the rest of the implant as well as providing suppleness which allows the hoops to deform over the Z-stent when the graft is compressed to fit in a delivery catheter.

Thus the present invention provides a design technique which allows the two reinforcing structures to be combined in a single device while allowing the entire device to be compressed and packed in delivery sheaths which are typically ¼ of the diameter of the device.

BRIEF DESCRIPTION OF THE DRAWINGS

A preferred embodiment of the present invention will now be described with reference to the drawings, in which.

DETAILED DESCRIPTION OF PREFERRED VERSIONS OF THE INVENTION

Figure 1:
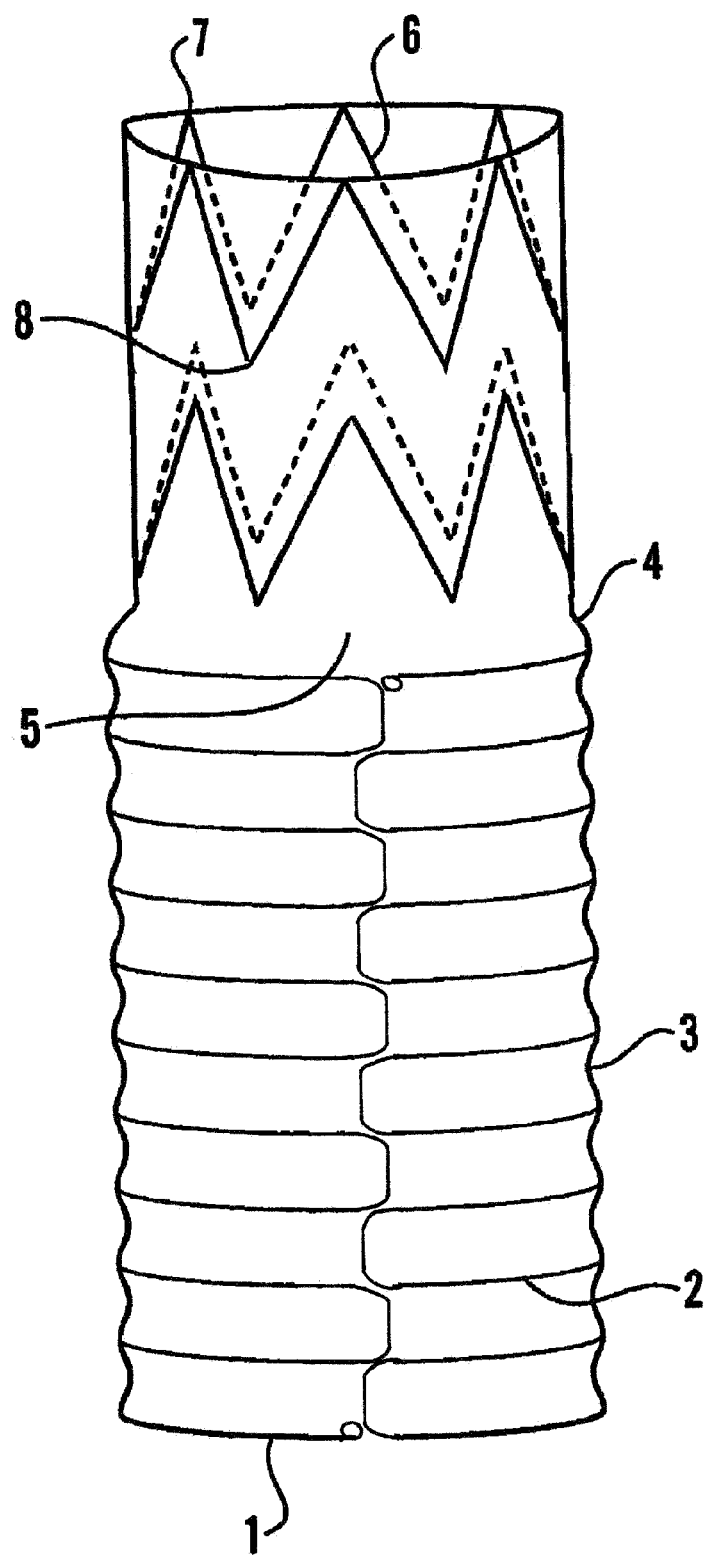
FIG. 1 depicts a tubular stent graft in accordance with the present invention.
Figure 2:
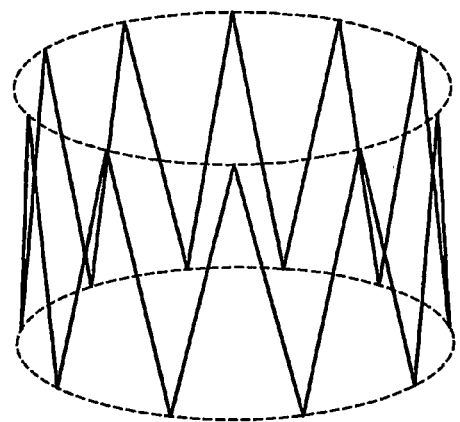
FIG. 2 depicts a generalised Z-stent as employed in prior art devices.
Figure 3A:
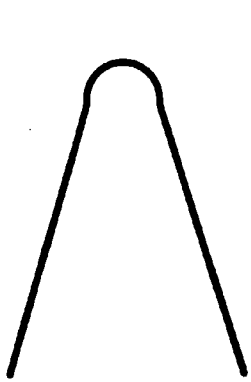
FIG. 3 depicts a series of bends which have been employed in prior art devices.
Figure 3B:
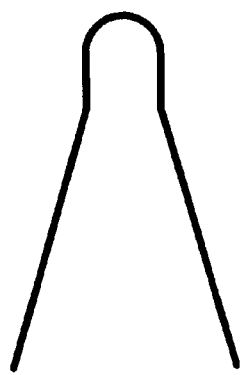
Figure 3C:
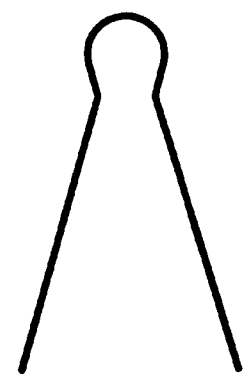
Figure 3D:
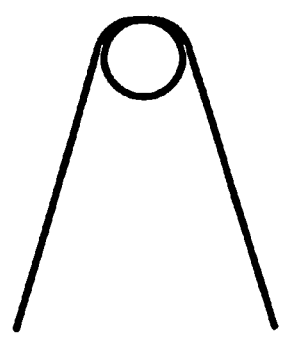

FIG. 1 illustrates the principle components of the design comprising:
The stent graft (1)
Reinforcing hoops (2)
Graft Fabric (3)
A change in diameter (4)

A spacing interval (5) between reinforcement hoops and the Z-stent

A Z-stent (6) comprising peaks (7) and troughs (8).

The embodiment shown in FIG. 1 shows the combination of a Z-stent (6) with reinforcing hoops (2) in a stent graft (1). The change in diameter (4) of the stent graft (1) is arranged so that the hoop reinforcements (2) can be deformed into a saddle shape so that they partially overlie the Z-stent (6) section of the implant. FIG. 1 illustrates the change in diameter (4) increasing from the Z-stent (6) section with a diameter of 30 mm to the hoop (2) section of the stent graft (1) which has a diameter of 32 mm.

The distance from the peaks (7) to the troughs (8) of Z-stent (6) is about 16 mm.

The axial length of the spacing interval (5) is about 7 mm.

The invention claimed is:

1. A stent graft for implantation in a body lumen comprising
   a tubular graft;
   a first stent section disposed on the tubular graft, the first stent section comprising reinforcing material formed into a first pattern;
   a second stent section disposed on the tubular graft, the second stent section comprising reinforcing material formed into a second pattern, the first pattern being different from the second pattern,
   the reinforcing material of the first and second stent sections being different from the material of the graft,
   wherein the reinforcing material of the first pattern is disposed on the tubular graft in a pattern which extends along and oscillates repeatedly across opposing sides of a line which is parallel to the longitudinal axis of the tubular graft,
   and wherein the reinforcing material of the second pattern includes circumferential hoops orbiting the longitudinal axis of the tubular graft and extending circumferentially about the circumference of the tubular graft, each hoop being separate and spaced from each other hoop,
   the tubular graft having a first diameter in the region of the first stent section and a second diameter in the region of the second stent section,
   wherein the first diameter is different from the second diameter.

2. The stent graft of claim 1 wherein the difference between the first diameter and the second diameter is up to 5 mm.

3. The stent graft of claim 1 wherein the difference between the first diameter and the second diameter is about 2 mm.

4. The stent graft of claim 1 wherein the first diameter is larger than the second diameter.

5. The stent graft of claim 1 wherein the second diameter is larger than the first diameter.

6. The stent graft of claim 1 wherein one or more of the circumferential hoops of the second stent section each oscillate repeatedly across a line running circumferentially around the circumference of the tubular graft, and orbiting the longitudinal axis of the tubular graft.

7. The stent graft of claim 6, wherein the ratio of the mean distance from
   (1) the peak to the trough of the oscillation measured parallel to the longitudinal axis of the graft diameter to
   (2) the diameter of the graft in the region of the second stent section is about 1:2.

8. The stent graft of claim 6 wherein the second stent section has 2+4n peaks wherein n is an integer ranging from 1 to 3.

9. The stent graft of claim 1 wherein the first and second stent sections are separated by a spacer section lacking reinforcing material, the axial length of which is from a sixth to a third of the diameter of the graft in the region of the first stent section.

10. The stent graft of claim 1 wherein the oscillations of the reinforcing material of the first pattern have amplitudes extending circumferentially across at least a major portion of the circumference of the first section, whereby the reinforcing material extends circumferentially across at least a major portion of the circumference of the first section and then reverses direction to extend circumferentially across at least a major portion of the circumference of the first section.

11. The stent graft of claim 1 wherein the oscillations of the reinforcing material of the first pattern each include:
    a. a longitudinal portion extending in a direction oriented primarily parallel to the longitudinal axis of the tubular graft, and
    b. circumferential portions extending from opposing ends of the longitudinal portion, the circumferential portions extending in a direction oriented primarily along the circumference of the tubular graft.

12. The stent graft of claim 11 wherein the reinforcing material of the first pattern is defined by a continuous length of wire.

13. The stent graft of claim 11 wherein one or more of the circumferential hoops of the second stent section each oscillate across opposing sides of a line running around the circumference of the tubular graft.

14. The stent graft of claim 13 wherein:
    a. the reinforcing material of the first pattern is defined by a continuous length of wire, and
    b. each of the circumferential hoops of the second stent section is defined by a continuous length of wire.

15. The stent graft of claim 1 wherein no oscillation of the reinforcing material of the first pattern crosses another oscillation of the reinforcing material of the first pattern to define circumferentially overlapping oscillations.

16. The stent graft of claim 1 wherein no portion of the reinforcing material of the first pattern crosses another portion of the reinforcing material of the first pattern, such that the reinforcing material of the first pattern does not overlap about the circumference of the first section.

17. A method comprising:
    a. radially compressing a stent graft having:
       (1) a tubular graft,
       (2) a first stent section disposed on the tubular graft, the first stent section having a first diameter, and including reinforcing material formed into a first pattern, the first pattern including a continuous length of reinforcing material which is disposed around the first stent section in a pattern which extends along and oscillates repeatedly across a line which is parallel to the longitudinal axis of the first stent section, and
       (3) a second stent section disposed on the tubular graft, the second stent section having a second diameter and including reinforcing material formed into a second pattern, the second pattern including at least one circumferential hoop of reinforcing material which oscillates repeatedly across a line running circumferentially around the longitudinal axis of the second stent section,
    and wherein:
       i. the reinforcing material of the first and second stent sections is different from the material of the graft,
       ii. the first stent section does not include reinforcing material formed into a pattern oscillating repeatedly across a line running circumferentially around the longitudinal axis, and iii. the second stent section does not include reinforcing material formed into a pattern oscillating repeatedly across a line running parallel to the longitudinal axis;
b. inserting the compressed stent graft into a catheter having an internal diameter which is less than the diameter of the first stent section of the stent graft.

18. The method of claim 17 wherein the internal diameter is less than about a quarter of the diameter of the first stent section of the stent graft.

19. A stent graft for implantation in a body lumen comprising
a tubular graft;
a first stent section defined along the tubular graft, the first stent section including reinforcing material formed into a first pattern;
a second stent section defined along the tubular graft, the second stent section including reinforcing material formed into a second pattern,
the reinforcing material of the first and second stent sections being different from the material of the graft,
wherein the first pattern includes a continuous length of reinforcing material which is disposed around the tubular graft in a pattern which extends along and circumferentially oscillates across opposing sides of a line which is parallel to the longitudinal axis of the tubular graft,
and wherein the second pattern includes at least one circumferential hoop of reinforcing material orbiting the longitudinal axis of the tubular graft, and which extends along and oscillates across opposing sides of a line running around the circumference of the tubular graft,
and wherein the first stent section does not include reinforcing material formed into a pattern oscillating across opposing sides of a line running around the circumference of the tubular graft, and the second stent section does not include reinforcing material formed into a pattern oscillating across opposing sides of a line running parallel to the longitudinal axis.

20. The stent graft of claim 19 wherein in the first pattern the ratio of the mean distance from the peak to the trough of said oscillation measured parallel to the longitudinal axis of the graft to the diameter of the graft in the region of the second stent section is about 1:2.

21. The stent graft of claim 19 wherein the second pattern has exactly 2+4n peaks wherein n is an integer ranging from 1 to 3.

22. The stent graft of claim 19 wherein the tubular graft has a first diameter in the region of the first stent section and a second diameter in the region of the second stent section, and wherein the first diameter is different from the second diameter.

23. The stent graft of claim 22 wherein the difference between the first diameter and the second diameter is up to 5 mm.

24. The stent graft of claim 22 wherein the difference between the first diameter and the second diameter is about 2 mm.

25. The stent graft of claim 19 wherein the first and second stent sections are separated by a spacer section lacking reinforcing material, the axial length of which is from a sixth to a third of the diameter of the graft in the region of the first stent section.

26. The stent graft of claim 19 wherein the second stent section includes two or more circumferential hoops of reinforcing material oscillating across opposing sides of a line running around the circumference of the tubular graft.

27. The stent graft of claim 26 wherein each of the circumferential hoops of the second stent section are separate and spaced from each other.

28. The stent graft of claim 19 wherein the oscillations of the reinforcing material of the first pattern have amplitudes extending circumferentially across at least a major portion of the circumference of the first section, whereby the reinforcing material extends circumferentially across at least a major portion of the circumference of the first section and then reverses direction to extend circumferentially across at least a major portion of the circumference of the first section.

29. The stent graft of claim 19 wherein no portion of the reinforcing material of the first pattern crosses another portion of the reinforcing material of the first pattern, whereby no portions of the reinforcing material of the first pattern define circumferentially overlapping oscillations.

* * * * *